United States Patent
Cho

(10) Patent No.: US 8,536,123 B2
(45) Date of Patent: Sep. 17, 2013

(54) USE OF BLOOD FLOW PARAMETERS TO MONITOR OR CONTROL THE DOSING OF ERYTHROPOIESIS-STIMULATING AGENTS

(75) Inventor: Daniel J. Cho, Chesterbrook, PA (US)

(73) Assignee: Health Onvector Inc., Pennsauken, NJ (US)

( * ) Notice: Subject to any disclaimer, the term of this patent is extended or adjusted under 35 U.S.C. 154(b) by 396 days.

(21) Appl. No.: 12/746,863

(22) PCT Filed: Jan. 9, 2009

(86) PCT No.: PCT/US2009/000117
§ 371 (c)(1),
(2), (4) Date: Jun. 14, 2010

(87) PCT Pub. No.: WO2009/089039
PCT Pub. Date: Jul. 16, 2009

(65) Prior Publication Data
US 2010/0261648 A1    Oct. 14, 2010

Related U.S. Application Data

(60) Provisional application No. 61/010,525, filed on Jan. 9, 2008.

(51) Int. Cl.
*A61K 38/18*   (2006.01)
*A61P 7/06*    (2006.01)
*C07K 14/505*  (2006.01)
*G01N 11/00*   (2006.01)

(52) U.S. Cl.
USPC .......................................... 514/7.7; 73/54.01

(58) Field of Classification Search
None
See application file for complete search history.

(56) References Cited

PUBLICATIONS

A. Besarab et al., "The Effects of Normal as Compared with Low Hematocrit Values in Patients with Cardiac Disease who are Receiving Hemodialysis and Epoetin", *The New England Journal of Medicine*, pp. 584-590 (1998).
K. Amann et al, "Myocyte/Capillary Mismatch in the Heart of Uremic Patients", *Journal of the American Society of Nephrology*, pp. 1018-1022 (1997).
O. Ifudu et al., "Erythropoietin-Induced Elevation in Blood Pressure is Immediate and Dose Dependent", *Nephron*, 79:486-487 (1998).
M.V. Kameneva et al., "Gender difference in rheologic properties of blood and risk of cardiovascular diseases", *Clinical Hemorheology and Microcirculation*, 21:357-363 (1999).
Patrick S. Parfrey et al., "Double-Blind Comparison of Full and Partial Anemia Correction in Incident Hemodialysis Patients without Symptomatic Heart Disease", *American Society of Nephrology*, 16:2180-2189 (2005).
T. Drueke et al., "Normalization of Hemoglobin Level in Patients with Chronic Kidney Disease and Anemia", *The New England Journal of Medicine*, 355(20):2071-2084 (2006).
A. Singh et al, "Correction of Anemia with Epoetin Alfa in Chronic Kidney Disease", *The New England Journal of Medicine*, 355(20):2085-2098 (2006).
R. Foley et al, "The Impact of Anemia of Cardiomyopathy, Morbidity, and Mortality in End-Stage Renal Disease", *American Journal of Kidney Diseases*, 28(1):53-61 (1996).
E. Friedman, "The relative contribution of measured variables to death risk among hemodialysis patients", *Death on Hemodialysis: Preventable or Inevitable*, Chapter 13:121-141 (1994).
National Kidney Foundation, "Clinical Practice Guidelines for the Treatment of Anemia of Chronic Renal Failure", *American Journal of Kidney Diseases*, 30(4)(Suppl. 3):192-240 (1997).
A.E.G. Raine, "Hypertension, Blood Viscosity, and Cardiovascular Morbidity in Renal Failure Implications of Erythropoietin Therapy", *The Lancet*, 1:97-100 (1988).

*Primary Examiner* — Marcela M Cordero Garcia
(74) *Attorney, Agent, or Firm* — Ostrolenk Faber LLP

(57) ABSTRACT

A method that includes a measurement of hemoglobin or hematocrit with a measurement of hemodynamic parameters to monitor and/or control a modality of treatment of a patient suffering from anemia.

3 Claims, 3 Drawing Sheets

USE OF BLOOD FLOW PARAMETERS TO MONITOR OR CONTROL THE DOSING OF ERYTHROPOIESIS-STIMULATING AGENTS

CROSS REFERENCE TO RELATED APPLICATIONS

The present application is a 35 U.S.C. §371 National Phase conversion of PCT/US2009/000117, filed Jan. 9, 2009, which claims benefit of U.S. Provisional Application No. 61/010,525, filed Jan. 9, 2008, the disclosure of which is incorporated herein by reference. The PCT International Application was published in the English language.

FIELD OF THE INVENTION

The present invention relates generally to the use of blood flow parameters such as whole blood viscosity and changes in whole blood viscosity to monitor or control the dosing of erythropoiesis-stimulating agents (or "ESAs").

GLOSSARY OF ABBREVIATIONS ckd=chronic kidney disease
crf=chronic renal failure
esa=erythropoiesis-stimulating agent
epo=erythropoietin
hct=hematocrit
hgb=hemoglobin
ami=acute myocardial infarction

REFERENCES

1—Singh A K, Szczech L, Tang K L, Barnhart H, Sapp S, Wolfson M, Reddan D; CHOIR Investigators. Correction of anemia with epoetin alfa in chronic kidney disease. N Engl J. Med. 2006 Nov. 16; 355(20):2085-98.
2—Drueke T B, Locatelli F, Clyne N, Eckardt K U, Macdougall I C, Tsakiris D, Burger H U, Scherhag A; CREATE Investigators. Normalization of hemoglobin level in patients with chronic kidney disease and anemia. N Engl J. Med. 2006 Nov. 16; 355(20):2071-84
3—Besarab A, Bolton W K, Browne J K, Egrie J C, Nissenson A R, Okamoto D M, Schwab S J, Goodkin D A. The effects of normal as compared with low hematocrit values in patients with cardiac disease who are receiving hemodialysis and epoetin. N Engl J. Med. 1998 Aug. 27; 339(9):584-90.
4—Parfrey P S, Foley R N, Wittreich B H, Sullivan D J, Zagari M J, Frei D. Double-blind comparison of full and partial anemia correction in incident hemodialysis patients without symptomatic heart disease. J Am Soc Nephrol. 2005 July; 16(7):2180-9
5—Lowrie E G, Ling J, Lew N L, Yiu Y. The relative contribution of measured variables to death risk among hemodialysis patients; in Friedman E A (ed): Death on Hemodialysis: Preventable or Inevitable? Boston, Kluwer, 1994, chap 13, pp 121-141.
6—Murray D C, Barre P E. The impact of anemia on cardiomyopathy, morbidity and mortality in end-stage renal disease. Am J Kidney Dis 1996; 28:53-61.
7—NKF-DOQI Work Group. NKF-DOQI clinical practice guidelines for the treatment of anemia of chronic renal failure. Am J Kid Dis 1997; 30:S192-240.
8—Ifudu O., Dawood M, Homel P. Erythropoietin-induced elevation in blood pressure is immediate and dose dependent. Nephron 1998; 79:486-487
9—Raine A E. Hypertension, blood viscosity, and cardiovascular morbidity in renal failure: Implications of erythropoietin therapy. The Lancet, 1998; Jan. 16; 97-100.
10—Amann K, Breitbach M, Ritz E, and Mall G. Myocyte/Capillary Mismatch in the Heart of Uremic Patients. J. American Soc. Nephrology, 1998; 9:1018-1022
11—Kameneva M V, Watach M J and Borovetz H S. Gender difference in rheological properties of blood and risk of cardiovascular diseases Clin. Hemorheology and Microcirculation, 1999; 21:357-363.

BACKGROUND OF THE INVENTION

Advanced kidney failure usually leads to anemia, primarily as a result of deficient renal erythropoietin production. There is increasing evidence that anemia is associated with the progression of left-ventricular hypertrophy, which is one of the most significant adverse risk factors in patients with chronic renal insufficiency. Left-ventricular hypertrophy predisposes to symptomatic cardiac failure and death.

Without the utilization of ESAs, lower hematocrit and hemoglobin levels have been associated with greater mortality rates for kidney failure patients on hemodialysis. It has been reported that the survival rates of patients may fall when the hematocrit falls below 30-33% [Lowrie et al., 1994]. It has also been reported that each one percent drop in hemoglobin can be associated with 14-19 percent increase in mortality [Murray et al. 1996].

These findings imply that the correction of renal anemia has the potential to improve patient prognosis. As such, most patients undergoing hemodialysis are at present treated with recombinant human erythropoietin (epoetin) to stimulate erythropoiesis to correct the anemia partially.

When erythropoietin was first approved by the US Food and Drug Administration ("FDA") during the late 1980's for use in dialysis patients, there was no firm scientific evidence to support recommended hemoglobin levels.

Over the past 20 years, the use of erythropoiesis-stimulating agents (ESAs) has been extended throughout the ever-expanding chronic kidney disease population. However clinical practice guidelines and target hemoglobin levels outlined by the Kidney Disease Outcomes Quality Initiative ("KDOQI") guidelines [NKF-KDOQI Work Group, 1997], which drive clinical practice, are still largely based on observational data. In 1997, the dialysis outcome and quality initiative ("DOQI") in the US recommended a target hematocrit range of 33-36% and hemoglobin targets of 11-12 g/dL [NKF-DOQI Work Group, 1997].

Based on the observational data, there has been a consensus building in the nephrology community that raising hemoglobin levels in chronic kidney disease patients is beneficial. These attitudes are based on observed improvements in quality-of-life parameters such as exercise tolerance and neurological function. The consensus was developed from a physiologic perspective that the higher hemoglobin targets for anemic patients reflected a normalization of hematocrit levels which would be associated with better outcomes among the anemic.

Hematocrit is the percentage of red blood cells in a blood sample volume. Hemoglobin is the oxygen-carrying molecule within red blood cells. Both are utilized as markers for the oxygen deliverability of a patient's blood. In general, adult males with a hematocrit of less than 41% and adult females with a hematocrit of less than 36% are considered anemic. The amount of hemoglobin in the blood is typically expressed in g/dL of blood (grams of hemoglobin per deciliter). The World Health Organization defines anemia as hemoglobin less than 12 g/dL for nonpregnant women and less than 13 g/dL for men.

Following the FDA approval of erythropoiesis-stimulating agents for use in the treatment of anemia associated with chronic renal failure ("CRF"), data from randomized, controlled clinical studies [Besarab et al. 1998, Singh et al. 2006, Drueke et al. 2006] showed increased rates of death and serious cardiovascular events when erythropoiesis-stimulating agents were administered for the purpose of achieving a higher hemoglobin concentration relative to a lower concentration.

Research performed by Besarab et al. [1998] was published as the Normal Hematocrit Study and rigorously tested the potential therapeutic advantages of higher hematocrit levels in certain dialysis patients. The Normal Hematocrit Study had a total of 1,265 patients with chronic renal disease on maintenance epoetin alfa, an ESA, with a hematocrit of 30±3% who were enrolled and randomized into group A (treatment group) or group B (control group). Group A patients received additional epoetin alfa during a correction phase to "normalize their hematocrit" to 42±3%, while patients in control group (B) remained on maintenance epoetin alfa (hematocrit: 30±3%). The primary objective of the study was to assess the effects of two different hematocrit target levels, 42% and 30%, on mortality and morbidity in hemodialysis patients with documented clinically evident cardiac disease [congestive heart failure (CHF) or ischemic heart disease] who were receiving epoetin alfa therapy. The primary endpoint was time-to-death or first non-fatal myocardial infarction. The final results of the study disclosed (Table 1 and FIG. 1) that dialysis patients normalized to a hematocrit of 42% ("normal hematocrit") experienced higher mortality and more non-fatal myocardial infarctions than patients targeting a hematocrit of 30%. The study was terminated early due to the detection of important safety considerations.

TABLE 1

Normal Hematocrit Primary Endpoint Components: Final Study Report

| Component | High Hct n = 634 | Low Hct n = 631 |
|---|---|---|
| Primary endpoint deaths | 208 (32.8%) | 173 (27.4%) |
| Total deaths | 221 (34.9%) | 185 (29.0%) |
| Non-fatal MI | 20 (3.2%) | 16 (2.5%) |

Hct = hematocrit

The CHOIR (Correction of Hemoglobin and Outcomes In Renal insufficiency) study [Singh et al. 2006] was conducted with the objective of comparing the composite cardiovascular event rates for chronic renal failure patients randomized into the following two groups: those having a target hemoglobin of 13.5 g/dL (group A; high hemoglobin group) versus those having a target hemoglobin of 11.3 g/dL (group B; low hemoglobin group). The hypothesis of the study was that in patients with chronic kidney disease, the use of recombinant human erythropoietin (epoetin alfa), an ESA, to achieve a higher hemoglobin level (13.5 g per deciliter) would decrease the risk of complications from cardiovascular causes and death, as compared with a lower hemoglobin level (11.3 g per deciliter). The physiologic approach of the working hypothesis was that higher hematocrit reflected a higher rate of perfusion of erythrocytes and improved oxygen delivery, metabolism and overall health. The primary efficacy outcome variable was a comparison of time-to-events for a composite primary endpoint integrating the following: mortality (all-cause mortality), CHF hospitalization (not including hospitalizations during which renal replacement therapy occurred), non-fatal stroke, and non-fatal myocardial infarction. Overall, 1432 patients were enrolled and randomized—715 to the higher hemoglobin group and 717 to the lower hemoglobin group. The study's primary endpoint showed a statistically significant disadvantage for patients in the higher hemoglobin group. Specifically, primary endpoint events occurred among 125 (17.5%) of patients in the higher hemoglobin group and 97 (13.5%) of patients in the lower hemoglobin group. Like the Normal Hematocrit Study, the CHOIR study was terminated before completion because the safety monitoring board determined that the study had little or no chance to demonstrate a benefit in the higher hemoglobin group. Baseline characteristics were generally similar between the two study groups, with the most common etiologies of renal failure relating to diabetes or hypertension. The time-to-event curves for the primary endpoint are shown in FIG. 2.

The CREATE ("Cardiovascular Risk Reduction by Early Anemia Treatment with Epoetin beta trial") study [Drueke et al. 2006], a third important study, was designed and conducted with parametric features similar to the CHOIR study. Specifically, the CREATE study randomized patients who were not undergoing dialysis to either a high hemoglobin target or a low hemoglobin target and also used a time-to-event analysis for a primary composite cardiovascular endpoint. In CREATE, 603 patients were randomized to a high hemoglobin target (13 to 15 g/dL) or a low hemoglobin target (10.5 to 11.5 g/dL). The primary endpoint was a composite of eight cardiovascular events: sudden death, myocardial infarction, acute heart failure, stroke, transient ischemic attack, angina pectoris resulting in hospitalization for 24 hours or more or prolongation of hospitalization, complication of peripheral vascular disease (amputation or necrosis), or cardiac arrhythmia resulting in hospitalization for 24 hours or more. Overall, a primary endpoint event occurred in 58 of 301 (19.3%) patients in the high hemoglobin group and 47 of 302 (15.6%) patients in the low hemoglobin group. Dialysis was required in more patients in the high hemoglobin group than in the low hemoglobin group (127 versus 111).

Potential adverse effects of anemia correction may be related to the increase in hemoconcentration as a result of fluid removal during dialysis. Hemoconcentration would effect rises in hematocrit and hemoglobin. As a relatively higher hemoglobin target level is associated with cardiac event risk, it is critical to be able to determine the optimum dose of erythropoiesis-stimulating agents for maximum benefit and minimum risk within the hemoconcentration framework.

SUMMARY OF THE INVENTION

A method according to the present invention utilizes blood flow parameters, specifically those incorporating whole blood viscosity measurements—such as intra-dialytic viscosity increase (or "viscosity surge" expressed, for example, as a percentage increase in whole blood viscosity), the ratio between hematocrit and viscosity, and the ratio between hemoglobin and viscosity—as tools for monitoring increases in hemoconcentration for the purpose of monitoring or controlling ESA dosages, whereby the safety and efficacy of the ESA may be improved.

Whole blood viscosity increases exponentially with rises in hematocrit. When, as a result of ESA administration and a raised hematocrit level, the viscosity of whole blood increases, the peripheral vascular resistance also increases ipso facto. In turn, blood pressure increases, a phenomenon which is known as recombinant erythropoietin (EPO)-induced hypertension in end-stage renal disease [Ifudu et al. 1998].

Life expectancy for patients with end-stage renal disease is approximately four years with a 22.5 percent annual mortality rate. Over half of all deaths of patients with end-stage renal failure are from cardiovascular disease, notably myocardial infarction, heart failure, and stroke, for which hypertension is a known risk factor. [Raine et al. 1998] These high cardiovascular event rates underscore the importance of erythropoietin-related hypertension. A method according to the present invention utilizes a physiologic approach that is centered on changes in blood flow parameters, especially those incorporating whole blood viscosity measurements—such as perfusion rates (oxygen perfusion, hematocrit perfusion, hemoglobin perfusion rates), shear stress and shear rate. A method according to the present invention connects ESA administration physiologically with hemoconcentration levels, as well as increased peripheral vascular resistance, blood pressure and cardiovascular risk.

Potential adverse effects of correcting anemia through the use of ESAs may also be related to the need for cotreatment with iron because most hemodialysis patients have functional iron deficiency such that iron availability for erythropoiesis is reduced. Iron is known to increase the level of oxidative stress in the body and thus related to the progression of atherosclerosis, acute myocardial infarction and cardiac death.

The goal of the erythropoiesis-stimulating agents (ESAs) is to maximize the tissue oxygen delivery rate or oxygen perfusion. Oxygen is carried by the hemoglobin molecules inside erythrocytes. As such, higher hematocrit and hemoglobin levels are often naturally assumed to reflect increased rates of oxygen perfusion at the tissue level. The above-mentioned studies considered only standard measures of hematocrit and/or hemoglobin to evaluate the oxygen delivery rate at tissue level.

The oxygen delivery rate at the tissue level, or oxygen perfusion rate, is far more accurately assessed by incorporating whole blood viscosity into the measure together with hematocrit or hemoglobin. The erythrocytes must be carried by blood. If the blood is very viscous, the blood cannot flow easily through a vessel. In particular, viscous blood moves very slowly at the tissue level because the diameters of the capillaries at the tissue level are very small. Most capillary vessels are 4-5 microns in diameter and arterioles have 30-50 microns in diameter.

Conditions of anemia are clinically defined as a hematocrit less than 41% for men and a hematocrit less than 36% for women. In terms of hemoglobin, anemia is assessed as hemoglobin values less than 12 g/dL for nonpregnant women and less than 13 g/dL for men. When a patient is anemic, that patient's blood contains fewer erythrocytes and is therefore less viscous. Therefore, even though the anemic patient's blood has lower hematocrit, hemoglobin and oxygen-carrying ability, the delivery and perfusion of oxygen at the tissue level may be higher because of reduced whole blood viscosity. This phenomenon represents a balancing act between hematocrit and hemoglobin on one hand and whole blood viscosity on the other. In a method according to the present invention blood flow parameters such as whole blood viscosity, or blood flow parameters that incorporate whole blood viscosity, such as the ratio between hematocrit and whole blood viscosity, as well as the ratio between hemoglobin and whole blood viscosity, are used for the purpose of monitoring or controlling the dosage of ESAs.

Several hemodynamic parameters, together with hematocrit and hemoglobin, affect the delivery of oxygen in the human body. Whole blood viscosity is an example of such hemodynamic parameters that can be used for the purpose of monitoring or controlling therapeutic modalities, particularly therapies that are applied for the correction of anemia or for maximizing oxygen delivery. Whole blood viscosity is a biological parameter that is very difficult to measure accurately across a range of shear rates, very poorly understood and generally overlooked by the medical community today.

Whole blood viscosity $\mu$ is a biological parameter that is inversely proportional to the blood flow rate, Q.

$$\mu = \pi d^4 \Delta P / 128 QL$$

where d is the inside diameter of a vessel, $\Delta P$ is the pressure drop along a finite length of the vessel, and L is the length of the vessel along the flow direction.

Mathematically, any means to reduce whole blood viscosity also increases the blood flow rate (or cardiac output) ipso facto. Oxygen is not only carried but also delivered by the blood through the circulatory system. Oxygen molecules are chemically bound to hemoglobin molecules inside erythrocytes, which move within whole blood. Since an increased blood flow rate means increased circulation of oxygen, reducing whole blood viscosity mollifies conditions of anemia assuming hematocrit and hemoglobin are held equal.

The blood flow rate Q is inversely proportional to blood viscosity $\mu$. Therefore, the ratio of hematocrit or hemoglobin to whole blood viscosity, not just the hematocrit or hemoglobin, is used in a method according to the present invention in order to correct conditions of anemia. These measurements are used in conjunction with the administration of ESAs for end-stage renal disease patients undergoing periodic hemodialysis.

A method according to the present invention allows for the improvement of the dosing of erythropoiesis-stimulating agents for chronic renal failure patients.

Measurement or control of blood flow parameters in the very same way improves the determination and dosing of any compound administered to chronic renal failure patients in the treatment of cardiovascular disease including cholesterol-reducing drugs, anti-thrombotic agents, anti-hypertensives and other cardiovascular agents.

In a method according to the present invention, blood flow parameters can be measured and used in conjunction with measurements of hematocrit or hemoglobin, glucose, lipids (LDL, HDL, and triglycerides) and measures of plasma proteins such as fibrinogen, C-reactive protein (CRP or hsCRP), homocysteine, and immunoglobulins as well as measurements of albumin.

Reductions in whole blood viscosity in this way can be used to increase functional capillary density, which is important for the oxygen delivery. The density of myocardial capillaries was shown to be significantly lower in dialyzed patients than in patients with essential hypertension or in normotensive control patients [Amann 1998]. Diminished left ventricular capillary supply in renal failure increases critical oxygen diffusion distance within the myocardium, thus exposing cardiomyocytes to the risk of hypoxia and eventually leading to myocardial infarction. As such, measurement of, control of and reductions in whole blood viscosity can be used in a method according to the present invention to prevent cardiac morbidity and mortality in end-stage renal disease patients. This is done in conjunction with improved administration and dosing of ESAs to end-stage renal disease patients.

Functional capillaries refer to capillary vessels wherein sufficient blood flow rate levels are maintained. When blood flow is not adequately maintained in a capillary, the small capillary vessel is called a non-functional capillary. If capillaries are non-functional over an extended period, the non-functional vessels disappear [Amann 1998]. The human body needs to have a sufficient number of functional capillaries to perfuse tissues. As such, the term functional capillary density is used to provide a quantitative estimate of blood perfusion status at the tissue level.

One method to increase the functional capillary density is through regular exercise. Such exercise forces the peripheral vessels at the tissue level to dilate, increasing blood flow through capillaries. With regular exercise, the number of the functional capillaries increases over time.

Another method to increase the functional capillary density is to reduce whole blood viscosity. When whole blood viscosity is reduced, blood flow in the non-functional capillaries can be improved and eventually restored. With reduced blood viscosity, the number of the functional capillaries increases over time.

The actual amount of oxygen delivered to a specific tissue depends on the product of the hematocrit and the blood volume flow rate at the specific location. Patients can be divided into three groups from the oxygen delivery point of view: one group of patients with a higher-than-normal hematocrit, one group with normal hematocrit, and the third group with a lower-than-normal hematocrit. The optimum hematocrit for the most efficient oxygen delivery in males may be in a range of 32-39% for adult males [Kameneva et al. 1999]. This optimum value is significantly lower than the normal reference value for males. The benefit of having a high hematocrit is that the blood contains a large amount of oxygen. However, since the high hematocrit causes blood as a whole to be more viscous, the blood may not be able to flow efficiently through the vasculature from the large arteries to the capillaries. Higher numbers of erythrocytes can also have a congestive effect within the vasculature. High hematocrit blood is more viscous and has an increased flow resistance than the blood with low hematocrit. This resistance to flow is pronounced in smaller vessels such as arterioles and capillaries, where oxygen delivery actually takes place.

Renal failure is a common complication of diabetes. In addition to renal failure, other complications of diabetic patients include cardiovascular diseases and stroke, occlusion of retinal vessels in the eye and blindness, and gangrene or non-healing skin ulcers in the lower extremities. Diabetics may frequently have anemia because of long-term use of pharmaceutical compounds and low erythropoietin levels, a state where the production of erythrocytes in the body in the bone marrow is hampered. Glucose imbalances in diabetic patients may aggravate conditions of anemia by increasing the stiffness of the erythrocyte membrane and reducing the deformability of the erythrocytes. As a result of reduced erythrocyte deformability, the viscosity of blood as a whole increases, also increasing its flow resistance. The anemia problem of diabetic patients is a challenging one because the blood often does not carry enough oxygen to begin with and is too thick to flow easily through small capillaries.

In order to monitor the treatment of anemia in diabetics that have had complications such as renal failure, a method according to the present invention uses measurements and/or control of hematocrit count or hemoglobin count on the one hand and hemodynamic parameters involving whole blood viscosity on the other hand in order to improve the safety and efficacy of other therapies that are being administered to the patient such as ESAs, whereby the other therapies can be better managed and ideally optimized.

Another aspect of the present invention is the use of blood flow parameters of whole blood viscosity, the ratio between hematocrit and viscosity, or the ratio between hemoglobin and viscosity—for the purpose of addressing or easing conditions of anemia, ischemia, pain and morbidity.

Another aspect of the present invention is the use of blood flow parameters of whole blood viscosity and percentage increase in viscosity during hemodialysis to monitor and control the safety, efficacy or dose of ESAs for the purpose of addressing or easing conditions of anemia and associated morbidity or mortality.

Another aspect of the present invention is the use of blood flow parameters of whole blood viscosity and percentage increase in viscosity during hemodialysis to monitor and control the hemoglobin target used in the dosing of ESAs for anemia correction in CRF patients.

A method according to the present invention includes monitoring or controlling therapeutic modalities using hemodynamic parameters such as whole blood viscosity, the ratio between hematocrit and viscosity, the ratio between hemoglobin and viscosity, and percentage increase in viscosity during hemodialysis. According to one aspect of the present invention, whole blood viscosity is used to monitor and/or to control the application, process, dosing, as well as the magnitude or frequency of a therapy that involves manipulation and variation of hemodynamic parameters. For example, in one embodiment, an active diagnostic-therapeutic full-loop apparatus may be deployed to manipulate hemodynamic parameters while monitoring and/or controlling the manipulation of the hemodynamic parameters. Optionally, the apparatus may be deployed to operate in real-time, meaning that blood is drawn from the patient and directly transferred to the apparatus for treatment, subjected to treatment, the treatment is monitored and/or controlled, and upon completion of the treatment, the treated blood is transferred back directly to the patient from the apparatus.

Other features and advantages of the present invention will become apparent from the following description of the invention which refers to the accompanying drawings.

DETAILED DESCRIPTION

Figure 1:
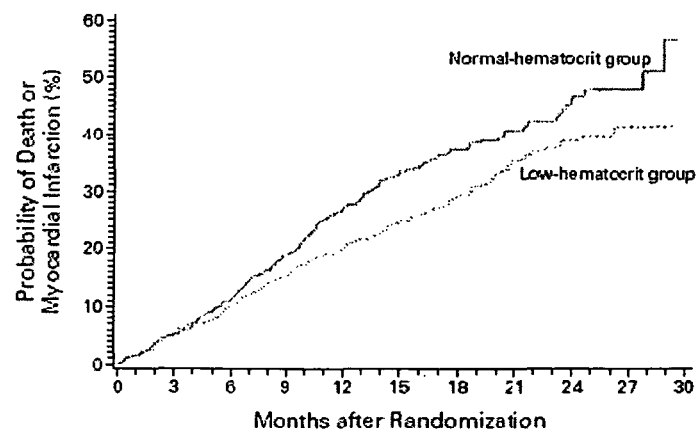
FIG. 1 graphically illustrates statistics relating to the probability of death due to myocardial infarction in a normal hematocrit group and a low hemotocrit group.

According to the present invention, a treatment modality of a patient suffering from anemia can be monitored based on the measurement of hematocrit or hemoglobin count on the one hand and on the other hand at least one hemodynamic parameter such as whole blood viscosity, plasma viscosity, intra-dialytic whole blood viscosity surge, and a combination of one hemodynamic parameter with another hemodynamic parameter, or with other hemodynamic parameters. The information obtained through the monitoring can be then used to adjust the treatment, if necessary, whereby the treatment method may be better controlled.

Thus, for example, one treatment modality for treating anemia, such as hemodialysis, can be monitored using a hemodynamic parameter such as whole blood viscosity, and the information obtained from the monitoring can be used to assess the safety and efficacy of another treatment modality such as the administration of an ESA to the patient. Alternatively, a treatment modality for treating anemia, such as the administration of an ESA can be monitored using a hemodynamic parameter, such as whole blood viscosity, and the information obtained can be used to monitor the safety an efficacy of another treatment modality such as hemodialysis. In yet another alternative, a treatment modality for treating anemia, such as hemodialysis or the administration of an ESA, can be monitored using a hemodynamic parameter such whole blood viscosity, and the information obtained can be used to assess the safety and efficacy of the treatment modality so that the treatment may be adjusted if necessary.

Thus, according to one embodiment of the invention, whole blood viscosity can be used to monitor and assess the efficacy and safety of an ESA in a patient under treatment for the correction of an anemic condition.

According to another embodiment of the invention, whole blood viscosity can be used to target the dose of a drug such as an ESA used to correct an anemic condition in a patient.

According to the preferred embodiment of the invention, intra-dialytic whole blood viscosity surge (that is the change in whole blood viscosity post-hemodialysis as compared with pre-hemodialysis) can be used to monitor and assess the efficacy and safety of an ESA in a patient suffering from anemia.

According to another embodiment of the invention, intra-dialytic viscosity surge can be used to target the dose of a drug such as an ESA used to correct an anemic condition in a patient.

ESA dosages are determined by nephrologists and their trained staff specifically for the purpose of achieving a target hemoglobin level to correct anemia.

In one embodiment of the invention, the intra-dialytic whole blood viscosity surge is used to modify the hemoglobin target. That is, the hemoglobin target used to determine the appropriate dose of an ESA for a patient can be evaluated by monitoring the intra-dialytic whole blood viscosity surge and adjusted in a patient under treatment for an anemic condition.

According to another embodiment of the invention the ratio of the hematocrit to whole blood viscosity measured at different shear rates can be used to determine the dosing of ESA in lieu of the hemoglobin target.

According to another embodiment of the invention the ratio of the hemoglobin to whole blood viscosity measured at different shear rates can be used to determine the dosing of ESA in lieu of the hemoglobin target.

Whole blood viscosity almost exponentially increases with hematocrit or hemoglobin as shown in FIG. 1.

Figure 2:
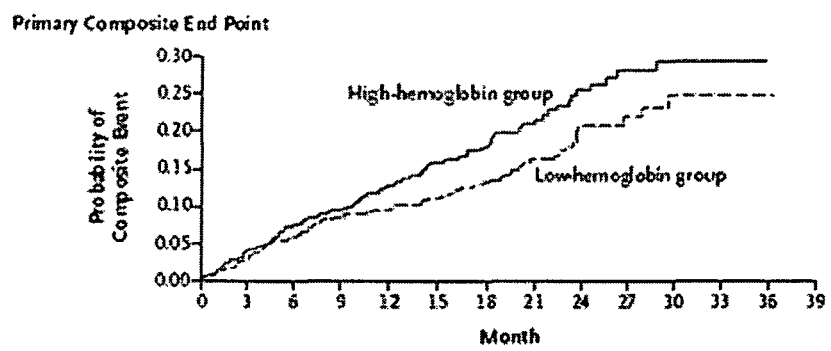
FIG. 2 graphically illustrates statistics relating to the probability of composite events in a high hemoglobin group and a low hemoglobin group.

The blood flow at tissue level involves flow through capillaries and arterioles, where blood moves relatively slowly. Therefore, the ratio of the hematocrit to whole blood viscosity at a low shear rate dictates the perfusion rate of blood at the tissue level. The data shown in FIG. 2 show that maximum peak value of this ratio occurs at a relatively wide range of hematocrit values between thirty and forty. The actual maximum peak value of this ratio varies from patient to patient, requiring the measurement of blood viscosity from each patient. Peak perfusion is a target value for the administration and dosing of ESAs, according to a preferred embodiment of the present invention. That is, in one preferred embodiment, once it has been determined that an adjustment of ESA is necessary in view of the measured whole blood viscosity values, a dosage likely to reach peak perfusion should be used.

Figure 3:
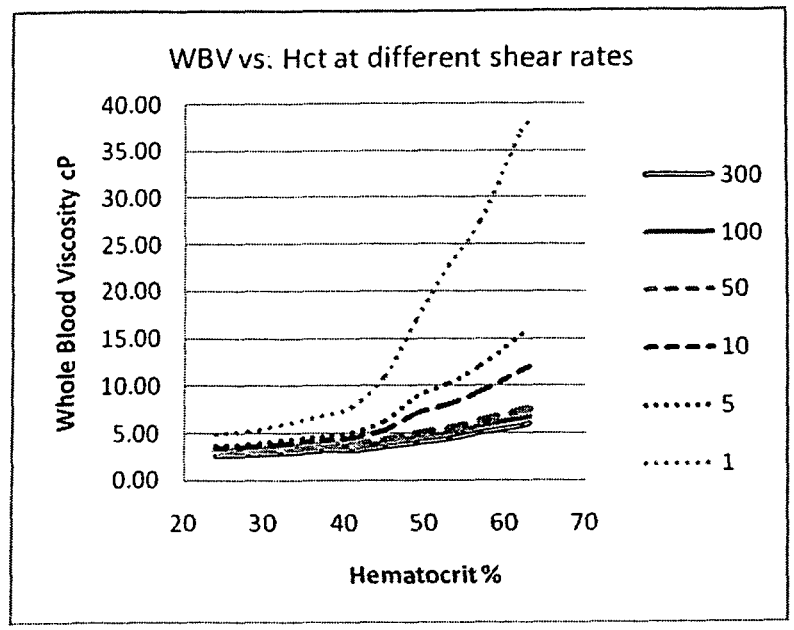
FIG. 3 is a graph of data demonstrating the relationship between hematocrit and whole blood viscosity at different shear rates.

FIG. 3 illustrates whole blood viscosity as a function of hematocrit at different shear rates (1-300 $s^{-1}$).

Figure 4:
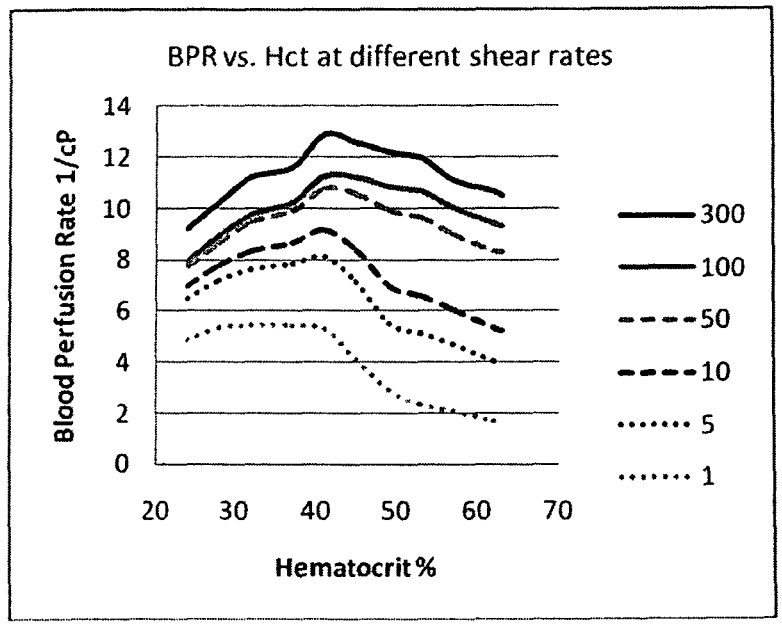
FIG. 4 illustrates blood perfusion rate as a function of hematocrit at different shear rates.

FIG. 4 illustrates blood perfusion rate, or ratio between hematocrit and viscosity, as a function of hematocrit at different shear rates (1-300 $s^{-1}$).

Figure 5:
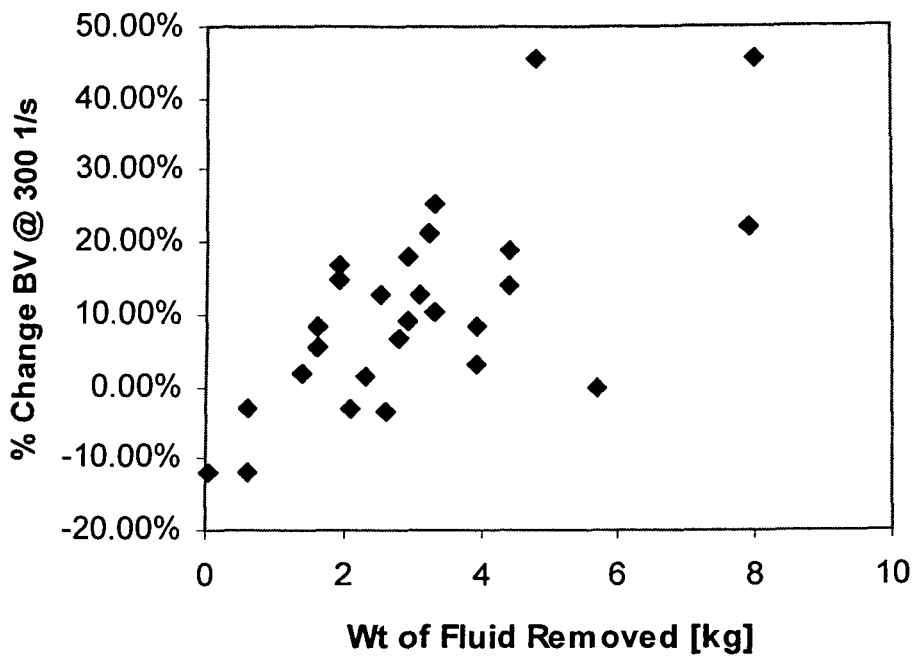
FIG. 5 is a graph of data plotting the difference between whole blood viscosity (measured at 300 $s^{-1}$) pre- and post-dialysis on the y-axis and the weight of the fluid removed during a given patient's dialysis session on the x-axis.

FIG. 5 plots the difference between whole blood viscosity pre- and post-hemodialysis on the y-axis and the weight of the fluid removed during a given patient's dialysis session on the x-axis. The whole blood viscosities at shear rates of 300 $s^{-1}$ of thirty dialysis patients were measured both pre- and post-hemodialysis for each patient. Dividing these 30 patients into 4 groups according to the patient's intra-dialytic viscosity changes: (i) 7% of patients experienced increases of whole blood viscosity by 47% or more; 43% of patients experienced increases of whole blood viscosity by 10-30%; 30% of patients experienced increases of whole blood viscosity by less than 10%; and 20% of patients experienced decreases in whole blood viscosity by 5-10%.

Figure 6:
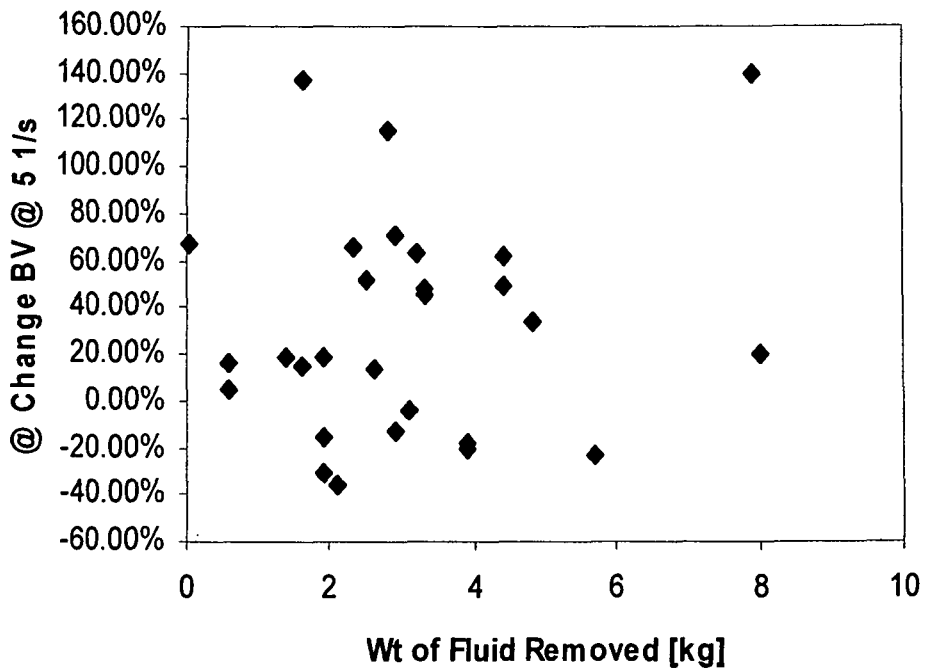
FIG. 6 is a graph of data plotting the difference between whole blood viscosity (measured at 5 $s^{-1}$) pre- and post-dialysis on the y-axis and the weight of the fluid removed during a given patient's dialysis session on the x-axis.

FIG. 6 plots the difference between whole blood viscosity at shear rates of 5 $s^{-1}$ pre- and post-hemodialysis on the y-axis and the weight of the fluid removed during a given patient's dialysis session on the x-axis. The whole blood viscosities at shear rates of 5 $s^{-1}$ of thirty dialysis patients were measured both pre- and post-hemodialysis for each patient. Approximately 40% of these patients had intra-dialytic whole blood viscosity surges (measured at 5 $s^{-1}$) of 40% or more.

The data presented in FIGS. 5 and 6 indicate that hemodialysis may have a profound and rather immediate effect on whole blood viscosity (i.e. cause a dramatic increase in whole blood viscosity) which, if not addressed can have dire consequences for the patient. For example, if the change in whole blood viscosity due to dialysis is not taken into account in administering another whole-blood-viscosity-increasing treatment (e.g. administration of ESA) then the patient may suffer greatly.

Thus, in one embodiment according to the present invention, whole blood viscosity values may be used to assess the need for the administration and dosing of epoetin and other ESAs. More specifically, patients having high intra-dialytic viscosity increases are administered lower doses of ESAs, while patients with large amounts of intra-dialytic fluid removal and inter-dialytic fluid weight gain, in particular, can be monitored more closely. The ratio between hematocrit and viscosity, as depicted in FIG. 4 (termed blood perfusion rate in the figure), can be also utilized under the present invention. Specifically, the peak value or peak inflection point of each patient's value as a function of ESA dosage, hematocrit and, or hemoglobin value can be targeted to obtain optimum results. ESAs are thereby administered with the use of blood flow parameters as a means of monitoring and assessing the need for change in the dosage of ESA.

According to an embodiment of the present invention, the whole blood viscosity of a patient who is being treated with an ESA is measured prior to dialysis, dialysis is carried out, shortly (before additional significant change in whole blood viscosity can take place, e.g., within 5 minutes of ceasing ultrafiltration or before whole blood viscosity can change by 5%) after dialysis the whole blood viscosity of the patient is measured again, the difference between the whole blood viscosity pre-hemodialysis and post-dialysis is determined (i.e. whole blood viscosity surge), and if the difference in the whole blood viscosity is judged to have crossed a threshold value, the dosage of ESA can adjusted (e.g. lowered). Thus, the change in the whole blood viscosity due to a treatment modality that can cause changes in the whole blood viscosity such as hemodialysis can be used to assess the need for modification of another treatment modality by discerning as to whether the first treatment modality has caused an adverse effect on the patient's whole blood viscosity and thus increased the risk of adverse effects by the second treatment modality. As a way of varying the dosage of ESA, the target hemoglobin may be changed. Alternatively, the ratio of hemoglobin to whole blood viscosity at different shear rates or the ratio of hematocrit to whole blood viscosity at different shear rates can be used instead of hemoglobin count as a target value.

In one specific implementation of the method, patients having intra-dialytic viscosity surges (measured at a low shear rate value such as 5 s$^{-1}$) of 40% or more would be designated as "high-surge" patients, whereas patients having intra-dialytic viscosity surges (measured again at a low shear rate value such as 5 s$^{-1}$) of less than 40% would be designated as "low-surge" patients. A hemoglobin target of 12 g/dL would be used for the low-surge patients, as is normally done for all dialysis patients. However, a hemoglobin target of 10 g/dL would be used for the high-surge patients, thereby adjusting the hemoglobin target as well as the subsequent ESA dose administration using the blood flow parameter.

In clinical practice, the hemoglobin levels of CRF patients undergoing hemodialysis are typically measured monthly or every other month. Such patients typically undergo dialysis 3-4 times per week. As such, the dosing of an ESA which can be delivered 3-4 times per week is based on a hemoglobin value that is measured once per month or every other month. Typically, the hemoglobin target is 12 g/dL, although a hemoglobin target of 13 g/dL is not unheard of in U.S. nephrology practice. In a specific implementation of a method according to the present invention, blood samples are drawn from CRF patients immediately before and immediately after dialysis. Those patients who have been designated as high-surge patients (i.e., those whose post-dialysis blood viscosity measurement is higher than the pre-dialysis viscosity measurement by more than a certain threshold value, such as 40%, 30%, or 20%), are administered ESA with a hemoglobin target of 10 g/dL rather than 12 g/dL. No adjustment in hemoglobin target is implemented for patients who do not have a high-surge in whole viscosity. The frequency of viscosity surge testing may be monthly or every other month as for hemoglobin, or alternatively, the frequency may be quarterly or biannually. Note that instead of a hemoglobin target, the ratio between hemoglobin and whole blood viscosity or the ratio between hematocrit and whole blood viscosity can be used as a target value for ESA dosing.

While in the preferred embodiment, hemodialysis is monitored using a hemodynamic parameter such as whole blood viscosity, other modes of treatment of an anemic condition can be monitored using a hemodynamic parameter such as whole blood viscosity in order to obtain information in order to assess the need for the modification of the same mode of treatment of the anemic condition or another mode of treatment of the anemic condition. For example, the change in whole blood viscosity that may be caused by administration of an ESA may be monitored and the information obtained can be used to assess the need to adjust hemodialysis of the patient, for example, to reduce the amount of fluid taken in a hemodialysis session when it is judged that the ESA has caused increase in the blood viscosity of the patient beyond a threshold value. Alternatively, if ESA has caused an increase in the value of the patient's whole blood viscosity a new target (e.g. a new hemoglobin count) can be set by varying the dosage of the ESA, or if hemodialysis has caused an increase in the whole blood viscosity of the patient beyond a threshold value, the effects of hemodialysis can be adjusted (e.g. reduce the fluid taken or add fluid to the patient's body) to prevent adverse consequences. Another treatment mode which may be monitored and/or adjusted according to the present invention by itself or in conjunction with another treatment mode is chemotherapy.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method for improving the safety and efficacy of an erythropoiesis-stimulating agent (ESA) in an anemic patient, comprising:
   treating an anemic patient with said ESA;
   measuring a whole blood viscosity of said anemic patient at a low shear rate to obtain a first viscosity value;
   performing hemodialysis on said patient;
   measuring a whole blood viscosity of said anemic patient at said low shear rate to obtain a second viscosity value;
   determining a value for a difference between said first viscosity value and said second viscosity value;
   comparing said value for said difference to a threshold value;
   targeting a hemoglobin count for said anemic patient if said value of said difference has crossed said threshold value; and
   administering an ESA dosage for said anemic patient to attain the targeted hemoglobin count.

2. The method of claim 1, wherein said difference is a percentage difference between said first viscosity value and said second viscosity value.

3. The method of claim 1, wherein said dosage is administered based on a ratio of hemoglobin count and whole blood viscosity of said patient at low shear rate.

* * * * *